United States Patent [19]

Hodge

[11] 4,224,246
[45] Sep. 23, 1980

[54] PROCESS FOR THE SYNTHESIS AND SEPARATION OF THE THREO AND ERYTHRO ISOMERS OF 2-AMINO-1-PHENYL-1-PROPANOL

[75] Inventor: Edward B. Hodge, Terre Haute, Ind.

[73] Assignee: International Minerals and Chemical Corporation, Terre Haute, Ind.

[21] Appl. No.: 914,269

[22] Filed: Jun. 12, 1978

Related U.S. Application Data

[63] Continuation-in-part of Ser. No. 743,813, Nov. 22, 1976, abandoned.

[51] Int. Cl.$^3$ ............................................. C07C 85/11
[52] U.S. Cl. .................................................. 260/570.6
[58] Field of Search .................................... 260/570.6

[56] References Cited

U.S. PATENT DOCUMENTS

| | | | |
|---|---|---|---|
| 2,347,621 | 4/1944 | Tindall | 260/584 |
| 3,775,479 | 11/1973 | Bruderer et al. | 260/570.6 X |

*Primary Examiner*—Robert V. Hines
*Attorney, Agent, or Firm*—Robert H. Dewey

[57] ABSTRACT

A process for the synthesis and separation of the threo and erythro isomers of 2-amino-1-phenyl-1-propanol comprising the steps of catalytically reducing 2-nitro-1-phenyl-1-propanol to form the acetate salt of the racemic mixture of 2-amino-1-phenyl-1-propanol and separating the isomers by fractional crystallization.

9 Claims, No Drawings

PROCESS FOR THE SYNTHESIS AND SEPARATION OF THE THREO AND ERYTHRO ISOMERS OF 2-AMINO-1-PHENYL-1-PROPANOL

CROSS-REFERENCE TO RELATED APPLICATIONS

This application is a continuation-in-part of applicant's copending application Ser. No. 743,813 filed Nov. 22, 1976 and now abandoned.

BACKGROUND OF THE INVENTION

This invention relates to an improved process for the production of phenyl amino alcohols. In a particular aspect, this invention relates to a method for selectively preparing the erythro and the threo isomers of diastereomeric phenylamino alcohols.

Phenylamino alcohols are widely used pharmaceuticals for vaso-constrictor activity, appetite suppressants and the like. Most of those in use contain an asymmetric carbon atom and exhibit optical activity. Many of the more useful ones, e.g. 2-amino-1-phenyl-1-propanol (phenylpropanolamine), have a second asymmetric carbon atom and also exist as diastereoisomers, namely the threo and erythro forms.

The threo and erythro forms generally produce different pharmacological responses. The threo form of racemic 2-amino-1-phenyl-1-propanol is active as an appetite suppressant but relatively weak as a vaso-constrictor. On the contrary, the erythro form (Propadrine) exhibits powerful vasoconstrictor activity. Accordingly, it has long been the practice to separate the diastereoisomers of such compounds when possible, though it is usually difficult and costly to do so, or to prepare the preferred isomer by a process which produces it exclusively.

Mixed isomers of 2-amino-1-phenyl-1-propanol can be readily prepared by reacting benzaldehyde with nitroethane in the presence of an alkaline catalyst to produce 2-nitro-1-phenyl-1-propanol and reducing the nitro group, as is known from F. W. Hoover and H. B. Hass, *J. Org. Chem.* 12, 506 (1947). This reaction gives excellent yields at low cost, but the mixture of isomers cannot be resolved satisfactorily to provide the erythro isomer in good yield. In fact, four recrystallizations were needed to prepare the erythro isomer of the hydrochloride of 2-amino-1-phenyl-1-propanol and they described the yield as "low".

Commercially, racemic, erythro 2-amino-1-phenyl-1-propanol (Propadrine) is usually prepared by reacting propiophenone with an alkyl nitrite to produce isonitrosopropiophenone which is reduced catalytically to the erythro isomer of the amine. This procedure, although satisfactory, is quite expensive. A need, therefore, exists for an improved process for selectively preparing erythro and threo isomers of diastereomeric phenylamino alcohols.

SUMMARY OF THE INVENTION

It is an object of this invention to provide an improved process for the production of phenylamino alcohols.

It is another object of this invention to provide an improved process for the selective production of the erythro and threo isomers of diastereomeric phenylamino alcohols.

Other objects will be apparent to those skilled in the art from the disclosure herein.

It is the discovery of this invention to directly produce and separate the threo and erythro isomers of 2-amino-1-phenyl-1-propanol by the steps of catalytically reducing 2-nitro-1-phenyl-1-propanol in a lower alkyl alcohol of from 1-4 carbon atoms in the presence of acetic acid to form the racemic mixture of the acetate salt of 2-amino-1-phenyl-1-propanol and separating the isomers thereof by crystallization of the threo isomer. The mother liquor is then acidified, reduced in volume and the acid salt of the erythro isomer is recovered therefrom by crystallization.

DETAILED DISCUSSION

The 2-nitro-1-phenyl-1-propanol used in the practice of this invention can be prepared by any suitable means, several of which are known. Suitable methods include that of J. Kamlet, U.S. Pat. No. 2,151,517 and F. W. Hoover and H. B. Hass referred to hereinbefore.

In the practice of this invention, the 2-nitro-1-phenyl-1-propanol is dissolved in a lower alkyl alcohol, preferably isopropyl alcohol. The mixture is placed in a vessel suitable for high pressure reactions and equipped with agitation means, e.g. a rocking bomb or a stirred bomb. Acetic acid is added to the solution to produce the acetate salt of 2-amino-1-phenyl-1-propanol during the reduction reaction.

The reduction reaction is performed at 500 psi hydrogen pressure in the presence of a suitable catalyst such as Raney nickel or palladium on char. Preferably, 5% palladium on char containing 50% water to make it safe is used as the catalyst for reduction. The mixture is reduced for three hours at a temperature of from about 60°–75° C. at 500 psi of hydrogen pressure. A temperature of about 75° C. is preferred for the reduction. Following the reduction, the mixture is filtered and the catalyst is washed with the lower alkyl alcohol solvent. The filtrate and wash are combined and concentrated at water pump vacuum to a pot temperature of about 60°–75° C. A pot temperature of about 75° C. is preferred. The residue is dissolved in hot lower alkyl alcohol, e.g. isopropyl alcohol, and the solution is allowed to cool at from about 2°–10° C. for about 6 to 8 hours. A precipitate forms during the cooling period. Filtration yields crystals of the acetate salt of 2-amino-1-phenyl-1-propanol which are about 84%–95% of the threo isomer as indicated by the nuclear magnetic resonance spectrum (NMR). If desired, the acetate salt can be readily converted to the hydrochloride, by known method, e.g. by treatment with a molar equivalent or more of hydrochloric acid, followed by reduction in volume by evaporation and crystallization of the chloride.

The mother liquor from the crystallization of the threo acetate contains the erythro isomer. It is acidified with concentrated acid, e.g. hydrochloric or sulfuric, preferably hydrochloric acid, and evaporated to about one third of its volume. It is then mixed with about a 1:1 by volume mixture of lower alkyl alcohol, e.g. isopropyl alcohol, and lower alkyl acetate, e.g. ethyl acetate. The mixture is then cooled, e.g. for about four hours, during which time a precipitate forms. Filtration gives crystals that are about 90–100% pure erythro salt, e.g. the hydrochloride or sulfate, of 2-amino-1-phenyl-1-propanol by NMR analysis. The salt can be purified by recrystallization from, e.g., isopropyl alcohol if desired.

The ability to separate the threo and erythro isomers of the acetate salts of 2-amino-1-phenyl-1-propanol by crystallization is unexpected, since both the threo and erythro isomers of the acetate have about the same solubility in isopropyl alcohol. In an experiment to determine the solubility of the two isomers in isopropyl alcohol, 5.0 g of the erythro isomer of 2-amino-1-phenyl-1-propanol acetate salt was dissolved in 50 ml of isopropyl alcohol. The mixture was cooled to 2°-10° C. for 6 to 8 hours, then filtered to give 4.1 g. The experiment was repeated with the exception that 2 ml of acetic acid were added. Upon filtration 3.8 g was obtained. The same two experiments were repeated in all essential detail using the threo isomer. The amounts recovered on filtration were identical to those obtained from the erythro isomer.

The process of the present invention will be better understood with reference to the following example. It is understood that the example is intended for illustration only and it is not intended that the invention be limited thereby.

EXAMPLE 1

A solution of 50.0 g of undistilled 2-nitro-1-phenyl-1-propanol in 600 ml of isopropyl alcohol plus 35 ml of acetic acid was reduced for three hours at 75° C. and 500 psi of hydrogen pressure in the presence of 8.0 g of 50% wet 5% palladium on char (Pd/C). The mixture was filtered and the catalyst was washed with 50 ml of isopropyl alcohol. The filtrate plus wash were concentrated at water pump vacuum to a pot temperature of 75° C. The residue was dissolved in 100 ml of hot isopropyl alcohol and the solution was cooled overnight in a refrigerator. Filtration gave 24.9 g (43%) of crystals melting at 145°-151° C. and indicated by NMR to be about 84% threo acetate salt of 2-amino-1-phenyl-1-propanol.

The filtrate was acidified with 13 ml of concentrated hydrochloric acid, evaporated to about 135 ml, mixed with 50 ml of isopropyl alcohol and 50 ml of 99% ethyl acetate and cooled for four hours. Filtration gave 12.8 g (24%) of crystals melting at 179°-190° C. NMR indicated this product to be about 90% erythro hydrochloride of 2-amino-1-phenyl-1-propanol.

The crude threo acetate was recrystallized from 200 ml of isopropyl alcohol to give 18.3 g (33%) of white crystals which melted at 149°-154° C. and analyzed 95% threo by NMR. More highly purified product melted at 152°-155° C. and analyzed 62.39% C, 8.02% H and 6.19% N. Calculated values are 62.53% C, 8.11% H and 6.63% N.

The crude erythro hydrochloride was also recrystallized from 200 ml of isopropyl alcohol to give 7.4 g (14%) of the erythro hydrochloride of 2-amino-1-phenyl-1-propanol which melted at 190°-193° C. and was indicated by NMR to be 95-100% pure.

I claim:

1. A process for the separation of a mixture of the erythro and threo isomers of 2-amino-1-phenyl-1-propanol obtained by the process of reducing 2-nitro-1-phenyl-1-propanol in the presence of acetic acid, thereby forming a reaction mixture containing the erythro and threo isomers of 2-amino-1-phenyl-1-propanol acetate salt, and separating the isomeric salt mixture, comprising the steps of:
   (a) forming a concentrated solution of the mixture of isomers in hot lower alkyl alcohol,
   (b) cooling at reduced temperature thereby forming crystalline threo 2-amino-1-phenyl-1-propanol acetate salt and separating same from the mother liquor containing the erythro isomer,
   (c) acidifying the mother liquor from step (b),
   (d) reducing volume of mother liquor to about one third,
   (e) adding a mixture of lower alkyl alcohol and lower alkyl acetate, and
   (f) cooling the mixture thereby resulting in formation of the crystalline salt of erythro 2-amino-1-phenyl-1-propanol.

2. The process of claim 1(b) wherein the solution is cooled at from 2°-10° C. for from about 6 to 8 hours.

3. The process of claim 1 wherein the acidification step is effected with hydrochloric acid.

4. The process of claim 1(a) wherein the lower alkyl alcohol is of from 1 to 4 carbon atoms.

5. The process of claim 4 wherein the alcohol is isopropyl alcohol.

6. The process of claim 1(e) wherein the lower alkyl alcohol is from 1 to 4 carbon atoms and the lower alkyl acetate is ethyl acetate, propyl acetate or isopropyl acetate.

7. The process of claim 6 wherein the alcohol is isopropyl alcohol and the acetate is ethyl acetate in a ratio of about 1:1 by volume.

8. A process for the synthesis and separation of the threo and erythro isomers of 2-amino-1-phenyl-1-propanol comprising the steps of catalytically reducing 2-nitro-1-phenyl-1-propanol, esterifying in the presence of acetic acid to form the acetate salt of the racemic mixture of 2-amino-1-phenyl-1-propanol and separating the isomers by fractional crystallization from isopropyl alcohol.

9. A process for the separation of a mixture of the acetate salts of the erythro and threo isomers of 2-amino-1-phenyl-1-propanol from a mixture containing them comprising the steps of:
   (a) forming a concentrated solution of the mixture of isomers in hot lower alkyl alcohol,
   (b) cooling the solution at reduced temperature thereby forming crystalline threo 2-amino-1-phenyl-1-propanol acetate salt and separating same from the mother liquor containing the erythro isomer.

* * * * *